United States Patent
Chen et al.

(10) Patent No.: US 8,268,562 B2
(45) Date of Patent: Sep. 18, 2012

(54) BIOMARKERS FOR PREDICTING RESPONSE OF ESOPHAGEAL CANCER PATIENT TO CHEMORADIOTHERAPY

(75) Inventors: Pei-Chun Chen, Taipei (TW); Yen-Ching Chen, Taipei (TW); Liang-Chuan Lai, Taipei (TW); Mong-Hsun Tsai, Taipei (TW); Shin-Kuang Chen, Taipei (TW); Pei-Wen Yang, Keelung (TW); Jang-Ming Lee, Taipei (TW); Eric Y. Chuang, Taipei (TW); Chuhsing K. Hsiao, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 12/582,357

(22) Filed: Oct. 20, 2009

(65) Prior Publication Data

US 2011/0091871 A1    Apr. 21, 2011

(51) Int. Cl.
*C12Q 1/68* (2006.01)
*C07H 21/04* (2006.01)
*C12P 19/34* (2006.01)

(52) U.S. Cl. .................. 435/6.11; 536/24.3; 435/91.2

(58) Field of Classification Search .................. None
See application file for complete search history.

(56) References Cited

OTHER PUBLICATIONS

Enzinger et al (The New England Journal of Medicine (2003) vol. 349, pp. 2241-2252).*
Benner et al (Trends in Genetics (2001) vol. 17, pp. 414-418).*
Yang et al (Clinical bioinformatics (2008) vol. 141, pp. 23-35).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Oxford dictionary of Biochemistry and Molecular biology (1997, pp. 152 and 282-283).*
Alakus, et al., "*GNAS1 T393C Polymorphism is Associated with Histopathological Response to Neoadjuvant Radiochemotherapy in Esophageal Cancer*", The Pharmacogenomics Journal (2009) 9, 202-207.
Nam, et al., "*Low hMLH1 Expression Prior to Definitive Chemoradiotherapy Predicts Poor Prognosis in Esophageal Squamous Cell Carcinoma*", Science Direct, Cancer Letters 260 (2008) 109-117.
Qin, et al, "Single-nucleotide Polymorphism-mass array reveals commonly deleted regions at 3p22 and 3p14.2 associate with poor clinical outcome in Esophageal Squamous Cell Carcinoma", Int. J. Cancer: 123, 826-830 (2008).
Chen, et al., "Two-stage Genome-wide Association Study for CCRT Response in Esophageal Cancer, Abstract of American Association for Cancer Research, 100th Annual Meeting, Apr. 18-22, 2009, Denver, Co, U.S.A.".

* cited by examiner

*Primary Examiner* — Steven Pohnert
(74) *Attorney, Agent, or Firm* — WPAT, P.C.; Anthony King

(57) ABSTRACT

The present invention relates to novel genetic markers associated with response of a patient with esophageal cancer (ECa) to chemoradiation therapy, and particularly to methods and kits for predicting an ECa patient's response to chemoradiation therapy by genotyping of the markers.

3 Claims, 1 Drawing Sheet

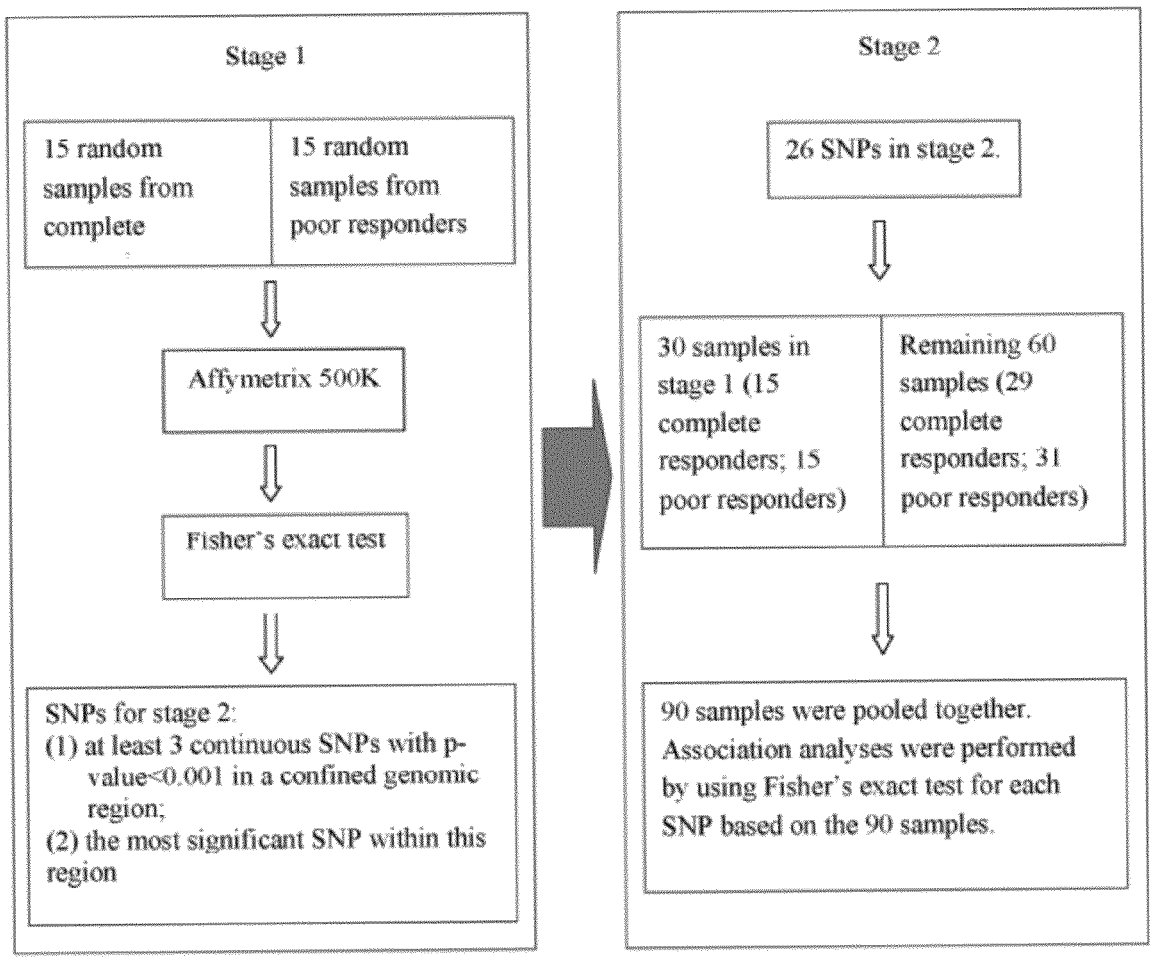

ns with esophageal cancer have advanced disease at the time of initial diagnosis and ineligible for curative surgical resection. Recently, multimodality therapies have been attempted to improve the resectability of tumors and the long-term survival of patients. Among them, concurrent chemoradiation therapy (CCRT) in a neoadjuvant setting followed by esophagogastrectomy has been widely applied in current clinical practice. However, it is found that individual variation in response to CCRT exists and is associated with different treatment outcomes. Patients with a complete response to CCRT tends to have an increased survival rate, but survival of patients without an evident response to CCRT may be compromised due to treatment-related toxicity and delays in surgical resection. Although studies have focused for biomarkers associated with the patients' response to chemoradiotherapy (*The pharmacogenomics journal* 2009; 9:202-7; *Cancer Lett* 2008; 260:109-17; and *Int J Cancer* 2008; 123:826-30), no reliable genetic markers are currently available.

There is still a need for a genetic marker that is predictive of an ECa patient's response to chemoradiotherapy, and thus helpful in preventing unnecessary treatments and determining the most appropriate treatment for patients.

BRIEF SUMMARY OF THE INVENTION

In one aspect, the present invention provides a method of predicting response of a patient suffering from esophageal cancer to chemoradiotherapy, which comprises genotyping a test sample from the patient for a single nucleotide polymorphism (SNP) marker selected from the group consisting of rs4954256 and rs16863886 and a combination thereof, wherein the presence of a C allele in rs4954256, a G allele in rs16863886 or both is indicative of an increased likelihood of having a complete response to chemoradiotherapy.

In another aspect, the present invention provides a kit for performing the method as described herein comprising one or more isolated polynucleotides for conducting the genotyping of rs4954256, rs16863886 or a combination thereof. In one embodiment, the kit comprises a first set of isolated polynucleotides for conducting the genotyping of rs16863886. In another embodiment, the kit comprises a second set of isolated polynucleotides for conducting the genotyping of rs4954256.

The various embodiments of the present invention are described in details below. Other characteristics of the present invention will be clearly presented by the following detailed description about the various embodiments and claims.

It is believed that a person of ordinary knowledge in the art where the present invention belongs can utilize the present invention to its broadest scope based on the description herein with no need of further illustration. Therefore, the following description should be understood as of demonstrative purpose instead of limitative in any way to the scope of the present invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the preferred embodiments shown.

In the drawings:

FIG. 1 shows an overview of the study design for the examples below.

DETAILED DESCRIPTION OF THE INVENTION

The present invention features two SNP markers, rs4954256 and rs16863886, identified by a two-stage genome-wide association study (GWAS), which are significantly associated with a complete CCRT response of an ECa patient and provide a high level of prediction accuracy.

Unless defined otherwise, all technical and scientific terms used herein have the meaning commonly understood by a person skilled in the art to which this invention belongs.

The articles "a" and "an" are used herein to refer to one or more than one (i.e., at least one) of the grammatical object of the article.

As used herein, the term "polynucleotide", "nucleic acid" or "nucleic acid molecule" refers to a polymer composed of nucleotide units, including naturally occurring nucleic acids, such as deoxyribonucleic acid ("DNA") and ribonucleic acid ("RNA") as well as nucleic acid analogs including those which have non-naturally occurring nucleotides. Polynucleotide can be synthesized, for example, using an automated DNA synthesizer. The term "nucleic acid" or "nucleic acid molecule" typically refers to a large polynucleotide. It will be understood that when a nucleic acid fragment is represented by a DNA sequence (i.e., A, T, G, C), this also includes an RNA sequence (i.e., A, U, G, C) in which "U" replaces "T."

As used herein, the term "isolated" with respect to nucleic acids, such as DNA or RNA, refers to molecules separated from other DNAs or RNAs, respectively, which are present in the natural source of the macromolecule. The term isolated as used herein also refers to a nucleic acid that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As used herein, the term "allele" refers to variants of a nucleotide sequence. A biallelic polymorphism has two forms. Diploid organisms may be homozygous or heterozygous for an allelic form.

As used herein, the term "SNP" refers to single nucleotide polymorphisms in DNA. SNPs are usually preceded and followed by highly conserved sequences that vary in less than 1/100 or 1/1000 members of the population. An individual may be homozygous or heterozygous for an allele at each SNP position. A SNP may, in some instances, be referred to as a "cSNP" to denote that the nucleotide sequence containing the SNP is an amino acid "coding" sequence. A SNP may arise from a substitution of one nucleotide for another at the polymorphic site. Substitutions can be transitions or transversions. A transition is the replacement of one purine nucleotide by another purine nucleotide, or one pyrimidine by another pyrimidine. A transversion is the replacement of a purine by a pyrimidine, or vice versa. For example, if at a particular chromosomal location, one member of a population has an adenine (A) and another member of the population has a cytosine (C) at the same position, then this position is a SNP. Alleles for SNP markers as referred to herein are expressed by the bases A, C, G or T as they occur at the polymorphic site in the SNP assay employed.

The nomenclature of SNPs as described herein refers to the official Reference SNP (rs) ID identification tag as assigned to each unique SNP by the National Center for Biotechnological Information (NCBI). The database is accessible to the public at www.ncbi.nlm.nih.gov/SNP/index.html.

As used herein, the term "genotype" means the identification of the alleles present in an individual or a sample. The term "genotyping" a sample or an individual for a genetic marker may comprise determination of which allele or alleles an individual carries for one or more SNPs. For example, a particular nucleotide in a genome may be an A in some individuals and a C in other individuals. Those individuals who have an A at the position have the A allele and those who have a C have the C allele. In a diploid organism the individual will have two copies of the sequence containing the polymorphic position. So the individual may have an A allele and a C allele, or alternatively two copies of the A allele, or two copies of the C allele. Each allele may be present at a different frequency in a given population. Those individuals who have two copies of the C allele are homozygous for the C allele and the genotype is CC, those individuals who have two copies of the A allele are homozygous for the A allele and the genotype is AA, and those individuals who have one copy of each allele are heterozygous and the genotype is AC.

As used herein, the terms "chemoradiation therapy," "chemoradiotherapy," "chemoirradiation" and "concurrent chemoradiation therapy (CCRT)" are interchangeable to refer to combination of chemotherapy and radiotherapy.

As used herein, the term "a complete response" to CCRT refers to complete remission of tumor without measurable symptoms such as microscopic residual tumor, grossly visible residual tumor, or progression of tumor.

As used herein, the term "primer" refers to a specific oligonucleotide sequence which is complementary to a target nucleotide sequence and used to hybridize to the target nucleotide sequence. A primer serves as an initiation point for nucleotide polymerization catalyzed by either DNA polymerase, RNA polymerase or reverse transcriptase.

As used herein, the term "probe" refers to a defined nucleic acid segment (or nucleotide analog segment, e.g., polynucleotide as defined herein) which can be used to identify a specific polynucleotide sequence present in samples, said nucleic acid segment comprising a nucleotide sequence complementary of the specific polynucleotide sequence to be identified.

In one aspect, the present invention provides a method of predicting response of a patient suffering from esophageal cancer to chemoradiotherapy comprising genotyping a test sample from the patient for a SNP marker selected from the group consisting of rs4954256, rs16863886 and a combination thereof, wherein the presence of a C allele in rs4954256, a G allele in rs16863886 or both is indicative of an increased likelihood of having a complete response to chemoradiotherapy.

Table 1 shows the naturally occurring nucleotide sequences (homo sapiens) containing rs4954256 (SEQ ID NO: 1) and the nucleotide sequences containing rs16863886 (SEQ ID NO: 2), obtained from the NCBI's database, wherein the nucleotide within the brackets is the polymorphic nucleotide. It shows that the polymorphic nucleotide of rs4954256 is located at position 27 of SEQ ID NO: 1, and the polymorphic nucleotide of rs16863886 is located at position 27 of SEQ ID NO: 2, respectively.

TABLE 1

| SNP | nucleotide sequences |
|---|---|
| rs4954256 | atattggagagttaacagagaatgcc[C/T]aaaactggaaaaacaaaaacttcaa (SEQ ID NO: 1) |
| rs16863886 | aatggtgtcccttgaaggctatctgt[C/T]tgcttttggataaaatggacagaag (SEQ ID NO: 2) |

SNP rs4954256 is located on chromosome 2q21.3 in ZRANB3, which belongs to the SMARCAL1 subfamily. The N-terminal of ZRANB3 contains a helicase followed by a zinc finger related to the Ran G protein binding proteins. However, the biological function of ZRANB3 is still unclear. SNP rs16863886 is located on chromosome 2q36.1 between SGPP2 and FARSB. FARSB encodes the phenylalanyl-tRNA synthetase beta subunit(s), which are regulatory subunits that form a tetramer with two catalytic alpha subunits. SGPP2 encodes an S1P (sphingosine-1-phosphate)-specific phosphohydrolase, which dephosphorylates S1P into Sphingosine. Both SGPP1 and ZRANB3 are involved in the G-protein function.

A test sample useful for practicing the method of the invention can be any biological sample of a patient with esophageal cancer that contains nucleic acid molecules, including portions of the gene sequences to be examined. As such, the sample can be a cell, tissue or organ sample, or can be a sample of a biological material such as blood, milk, tears, saliva, hair, skin, tissue, and the like. A nucleic acid sample useful for practicing a method of the invention can be DNA or RNA, particularly genomic DNA or an amplification product thereof. A specific example of a test sample in accordance with the invention is a blood sample.

In one embodiment, the method of the invention is conducted by genotyping a test sample of a patient with esophageal cancer for rs4954256 wherein the presence of a C allele in the SNP marker is indicative of an increased likelihood of having a complete response to chemoradiotherapy.

In another embodiment, the method of the invention is conducted by genotyping a test sample of a patient with esophageal cancer for rs16863886 wherein the presence of a G allele in the SNP marker is indicative of an increased likelihood of having a complete response to chemoradiotherapy.

In yet another embodiment, the method of the invention is conducted by genotyping a test sample of a patient with esophageal cancer for a combination of rs4954256 and rs16863886 wherein the presence of both a C allele in rs4954256 and a G allele in rs16863886 is indicative of an increased likelihood of having a complete response to chemoradiotherapy.

In particular, the patient evaluated for a likelihood of having a complete response to chemoradiotherapy in accordance with the method of the invention is a human adult with esophageal cancer. Typically, the patients are 18 years or older but younger than 70 years old. In certain embodiments, the patients are older than 25, 35, 45 or 55 but younger than 70 years old. In addition, in certain embodiments, the patient as described herein is an Asian patient, particularly a Chinese or Japanese patient. In certain embodiments, the patient is a man.

Numerous methods are known in the art for determining the nucleotide occurrence for a specific SNP in a sample. Such methods can utilize one or more oligonucleotide probes or primers, including, for example, an amplification primer pair that selectively hybridizes to a target polynucleotide, which corresponds to one or more SNP positions. Oligonucleotide probes useful in practicing a method of the invention can include, for example, an oligonucleotide that is complementary to and spans a portion of the target polynucleotide, including the position of the SNP, wherein the presence of a specific nucleotide at the position (i.e., the SNP) is detected by the presence or absence of selective hybridization of the probe. Such a method can further include contacting the target polynucleotide and hybridized oligonucleotide with an endonuclease, and detecting the presence or absence of a cleavage product of the probe, depending on whether the nucleotide occurrence at the SNP site is complementary to the corresponding nucleotide of the probe.

An oligonucleotide ligation assay also can be used to identify a nucleotide occurrence at a polymorphic position, wherein a pair of probes that selectively hybridize upstream and adjacent to and downstream and adjacent to the site of the SNP, and wherein one of the probes includes a terminal nucleotide complementary to a nucleotide occurrence of the SNP. Where the terminal nucleotide of the probe is complementary to the nucleotide occurrence, selective hybridization includes the terminal nucleotide such that, in the presence of a ligase, the upstream and downstream oligonucleotides are ligated. As such, the presence or absence of a ligation product is indicative of the nucleotide occurrence at the SNP site. An example of this type of assay is the SNPlex System (Applied Biosystems, Foster City, Calif.).

An oligonucleotide also can be useful as a primer, for example, for a primer extension reaction, wherein the product (or absence of a product) of the extension reaction is indicative of the nucleotide occurrence. In addition, a primer pair useful for amplifying a portion of the target polynucleotide including the SNP site can be useful, wherein the amplification product is examined to determine the nucleotide occurrence at the SNP site. In this regard, useful methods include those that are readily adaptable to a high throughput format, to a multiplex format, or to both. The primer extension or amplification product can be detected directly or indirectly and/or can be sequenced using various methods known in the art. Amplification products which span a SNP can be sequenced using traditional sequence methodologies such as the "dideoxy-mediated chain termination method," also known as the "Sanger Method" and the "chemical degradation method," also known as the "Maxam-Gilbertmethod."

Medium to high-throughput systems for analyzing SNPs, known in the art such as the Mass Array™ system (Sequenom, San Diego, Calif.), the BeadArray™ SNP genotyping system (San Diego, Calif.), Affymetrix GeneChip® Human Mapping 500K arrays (Affymetrix, Inc., Santa Clara, Calif.), can be used with the present invention.

The SNP detection methods for practicing the present invention typically utilize selective hybridization. As used herein, the term "selective hybridization" or the like refers to hybridization under moderately stringent or highly stringent conditions so that a nucleotide sequence preferentially associates with a selected nucleotide sequence over unrelated nucleotide sequences to a large enough extent to be useful in identifying a nucleotide occurrence of a SNP. It will be recognized that some amount of non-specific hybridization is unavoidable, but is acceptable provide that hybridization to a target nucleotide sequence is sufficiently selective such that it can be distinguished over the non-specific hybridization, for example, at least about 2-fold more selective, generally at least about 3-fold more selective, usually at least about 5-fold more selective, and particularly at least about 10-fold more selective, as determined, for example, by an amount of labeled oligonucleotide that binds to target nucleic acid molecule as compared to a nucleic acid molecule other than the target molecule, particularly a substantially similar (i.e., homologous) nucleic acid molecule other than the target nucleic acid molecule. Conditions that allow for selective hybridization can be determined empirically, or can be estimated based, for example, on the relative GC:AT content of the hybridizing oligonucleotide and the sequence to which it is to hybridize, the length of the hybridizing oligonucleotide, and the number, if any, of mismatches between the oligonucleotide and sequence to which it is to hybridize (see, for example, Sambrook et al., 2001, *Molecular Cloning: A Laboratory Manual, Third Edition*, Cold Spring Harbor Laboratory Press, Cold Spring Harbor, N.Y.; and *Current Protocols in Molecular Biology* (Ausubel et al., ed., J. Wiley & Sons Inc., New York, 1988).

Generally, stringent conditions are selected to be about 5-30° C. lower than the thermal melting point ($T_m$) for the specified sequence at a defined ionic strength and pH. Alternatively, stringent conditions are selected to be about 5-15° C. lower than the $T_m$ for the specified sequence at a defined ionic strength and pH. For example, stringent hybridization conditions will be those in which the salt concentration is less than about 1.0 M sodium (or other salts) ion, typically about 0.01 to about 1 M sodium ion concentration at about pH 7.0 to about pH 8.3 and the temperature is at least about 25° C. for short probes (e.g., 10 to 50 nucleotides) and at least about 55° C. for long probes (e.g., greater than 50 nucleotides). An exemplary non-stringent or low stringency condition for a long probe (e.g., greater than 50 nucleotides) would comprise a buffer of 20 mM Tris, pH 8.5, 50 mM KCl, and 2 mM $MgCl_2$, and a reaction temperature of 25° C.

According to the invention, the method as described herein can be used to determine if a patient with esophageal cancer exhibits an increased likelihood of having a complete response to chemoradiotherapy based on the genotype(s) of rs4954256 and/or rs16863886. As demonstrated in the examples below, each of a C allele in rs4954256 and a G allele in rs16863886 is a protective allele which is more frequently present in a population of patients having a complete response to chemoradiotherapy compared to a population of patients that do not have a complete response to chemoradiotherapy, and therefore the presence of a C allele in rs4954256 or a G allele in rs16863886 indicates that the patients has an increased possibility of having a complete response to chemoradiotherapy. Particularly, a patient exhibits a greater possibility (e.g. at least 1.5-, 2.0-, 2.5-, 3.0-, 3.5-, 4.0-, 4.5-, or 5.0-fold risk) of having a complete response as the number of a C allele in rs4954256 or a G allele in rs16863886 increases. More particularly, a patient exhibits an about 4.54-fold chance of complete chemoradiotherapy response as the number of the C allele in rs4954256 increases, and an about 3.84-fold chance of complete chemoradiotherapy response as the number of the G allele increases.

Isolated polynucleotides, serving as primers or probes, for example, can be used to perform the genotyping for the SNPs in accordance with the invention, which can readily be determined using the information regarding SNPs and associated nucleic acid sequences provided herein. A number of computer programs such as SeqTool Document v1.0 (IBMS, Taiwan) can be used to rapidly obtain optimal primer/probe sets. In one specific example, a first pair of primers is used to perform the genotyping of rs4954256 which have SEQ ID NOS: 3 and 4, respectively. In another specific example, a second pair of isolated polynucleotides is used to perform the genotyping of rs16863886 which have SEQ ID NOS: 5 and 6, respectively. Table 2 shows the sequences of the primers.

TABLE 2

| Primers | nucleotide sequences |
|---|---|
| rs4954256 | |
| forward primer | 5'-ACGTTGGATGTCTACCGTTTCCCGTATCTC-3' (SEQ ID NO: 3) |
| reverse primer | 3'-ACGTTGGATGCCATATTGGAGAGTTAACAG-5' (SEQ ID NO: 4) |
| rs16863886 | |
| forward primer | 5'-ACGTTGGATGCTGCTTAAGGCAATGGTGTC-3' (SEQ ID NO: 5) |
| reverse primer | 3'-ACGTTGGATGTTACTTTGGCCCTTCTGTCC-5' (SEQ ID NO: 6) |

In another aspect, the invention also provides a kit for performing the method as described herein comprising one or more isolated polynucleotides for conducting the genotyping of rs4954256, rs16863886 or a combination thereof. Particularly, the isolated polynucleotides are used as primers or probes for conducting the genotyping of the SNPs in accordance with the invention.

In some embodiments, the kits are PCR kits. In one example, the PCR kit includes the following: (a) primers used to amplify a SNP as describe herein; and (b) buffers and enzymes including DNA polymerase.

In some embodiments, the kits are microarray kits. The kits generally comprise probes attached to a solid support surface. The probes may be labeled with a detectable label. In a specific embodiment, the probes are specific for a SNP as described herein. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own a suitable container.

Primers or probes can readily be designed and synthesized by one of skill in the art for the nucleic acid region of interest. It will be appreciated that suitable primers or probes to be used with the invention can be designed using any suitable method.

A primer or probe is typically at least about 8 nucleotides in length. In one embodiment, a primer or a probe is at least about 10 nucleotides in length. In a specific embodiment, a primer or a probe is at least about 12 nucleotides in length. In another specific embodiment, a primer or probe is at least about 16, 17, 18, 19, 20, 21, 22, 23, 24 or 25 nucleotides in length. While the maximal length of a probe can be as long as the target sequence to be detected, depending on the type of assay in which it is employed, it is typically less than about 50, 60, 65, or 70 nucleotides in length. In the case of a primer, it is typically less than about 30 nucleotides in length. In a specific embodiment, a primer or a probe is within the length of about 18 and about 28 nucleotides. However, in other embodiments, such as nucleic acid arrays and other embodiments in which probes are affixed to a substrate, the probes can be longer, such as on the order of 30-70, 75, 80, 90, 100, or more nucleotides in length.

In one example, the kit of the invention comprises a first set of isolated polynucleotides for identifying the polymorphic nucleotide at rs4954256. Specifically, the isolated polynucleotides are primers having SEQ ID NOS: 3 and 4, respectively. In another example, the kit of the invention comprises a second set of isolated polynucleotides for identifying the polymorphic nucleotide at rs16863886. Specifically, the isolated polynucleotides are primers having SEQ ID NOS: 5 and 6, respectively. In yet another example, the kit of the invention comprises both a first set and a second set of isolated polynucleotides as above described.

According to the invention, the kit may further contain other agents used to detect the genetic polymorphisms such as (1) reagents for purifying nucleic acids; (2) dNTPs, optionally with one or more uniquely labeled dNTPs; (3) post synthesis labeling reagents, such as chemically active derivatives of fluorescent dyes; (4) enzymes, such as reverse transcriptases, DNA polymerases, and the like; (5) various buffer mediums, e.g., hybridization and washing buffers; (6) labeled probe purification reagents and components, like spin columns, etc.; and (7) signal generation and detection reagents, e.g., streptavidin-alkaline phosphatase conjugate and the like.

In some examples, the kit of the invention further comprises instructions for detecting the SNPs and evaluating the results. Specifically, the instructions describes that the presence of a C allele in rs4954256 or a G allele in rs16863886 as a result of the genotyping is indicative of an increased possibility of having a complete response to chemoradiotherapy. More specifically, the instructions describes that a patient evaluated exhibits an about 4.54-fold chance of complete chemoradiotherapy response as the number of the C allele in rs4954256 increases, and an about 3.84-fold chance of complete chemoradiotherapy response as the number of the G allele increases.

The various embodiments of the present invention are described in details below. Other characteristics of the present invention will be clearly presented by the following detailed description about the various embodiments and claims.

Example 1

Patient Population and Therapy

This study included ninety (90) ECa patients, males younger than 70 years, who received neoadjuvant CCRT followed by esophagectomy at the National Taiwan University Hospital. Informed consent was obtained from each subject and this study was approved by the institutional review board at National Taiwan University Hospital. Peripheral blood samples were drawn for each patient before surgery and chemoirradiation. Peripheral white blood cells were isolated and stored for further examination.

CCRT was conducted using the cisplatin-based regimen (6 mg/m$^2$ on day 1 and day 5 each week) plus 5-fluorouracil (225 mg/m$^2$ per day) and/or paclitaxel (35 mg/m$^2$ on day 1 and day 4 each week) with concomitant 4000 cGy of irradiation. The neoadjuvant irradiation was delivered using a standard antero-posterior/postero-anterior field technique. Four to six weeks after CCRT, esophagectomy and esophageal reconstruction with gastric or colonic interposition was performed for patients with resectable tumors and acceptable surgical risk according to cardiopulmonary function, nutritional status and general performance status.

Based on the pathologic evaluation of the surgical specimen, patients receiving CCRT were then categorized into two groups, complete responders for which pathologically complete remission was observed, and poor responders for which grossly visible residual tumor and/or progression of tumor was observed. Table 3 summarizes the clinical characteristics of the 90 patients.

TABLE 3

|  | Total Patients (n = 90) | |
|---|---|---|
|  | Complete responders (n = 44) | Poor responders (n = 46) |
| Age (years) | | |
| mean | 55.20 | 54.87 |
| SD | 7.2836 | 8.2263 |
| Cigarette smoking | | |
| Yes | 32 | 31 |
| No | 7 | 6 |
| Missing | 5 | 9 |
| Alcohol consumption | | |
| Yes | 32 | 31 |
| No | 7 | 6 |
| Missing | 5 | 9 |
| Betel nut chewing | | |
| Yes | 13 | 12 |
| No | 26 | 25 |
| Missing | 5 | 9 |

Example 2

Two-Stage Genome-Wide Association Study (GWAS)

A two-stage GWAS was performed to identify markers for predicting CCRT response in ECa patients. FIG. 1 shows an overview of the study design.

Stage 1

About 30% of the study population was included in Stage 1 as recommended in *Nat Genet* 2006; 38:209-13. Therefore, 15 patients each were randomly drawn from the CCRT complete responders (n=44) and poor responders (n=46), respectively. Table 4 summarizes the clinical characteristics of the 30 patients and those of remaining 60 patients.

TABLE 4

|  | Patients in Stage 1 (n = 30) | | Remaining patients (n = 60) | |
|---|---|---|---|---|
|  | Complete responders (n = 15) | Poor responders (n = 15) | Complete responders (n = 29) | Poor responders (n = 31) |
| Age (years) | | | | |
| mean | 55.67 | 54.6 | 54.97 | 55 |
| SD | 6.2526 | 7.8944 | 7.8580 | 8.5049 |
| Cigarette smoking | | | | |
| Yes | 11 | 10 | 21 | 21 |
| No | 2 | 3 | 5 | 3 |
| Missing | 2 | 2 | 3 | 7 |
| Alcohol consumption | | | | |
| Yes | 11 | 10 | 21 | 21 |
| No | 2 | 3 | 5 | 3 |
| Missing | 2 | 2 | 3 | 7 |
| Betel nut chewing | | | | |
| Yes | 4 | 5 | 9 | 7 |
| No | 9 | 8 | 17 | 17 |
| Missing | 2 | 2 | 3 | 7 |

Genomic DNA extracted from blood samples were isolated by proteinase K-phenol-chloroform extraction following standard protocols with 0.5% SDS and 200 µg/ml proteinase K. Total genomic DNA (250 ng) was digested with a restriction enzyme (Nsp I or Sty I) and ligated to adaptors that recognize the cohesive four base-pair (bp) overhangs. All fragments resulting from restriction enzyme digestion, regardless of size, were substrates for adaptor ligation. A generic primer that recognizes the adaptor sequence was used to amplify adaptor-ligated DNA fragments. PCR conditions had been optimized to preferentially amplify fragments in the 200 to 1,100 bp size range. The amplified DNA was then fragmented, labeled, and hybridized to GeneChip® Human Mapping 500K arrays (Affymetrix, Inc., Santa Clara, Calif.). After 16 hours of hybridization at 49° C., the arrays were washed by Fluidics Station 450 and scanned by GeneChip Scanner 3000.

Fisher's exact test was used to investigate the association between individual SNP and the CCRT response. Based on the two criteria (1) at least three continuous SNPs with a p-value<0.001 in a confined genomic region; and (2) the most significant SNP within this region (*Prostate* 2006; 66:1556-64), twenty-six (26) candidate SNPs were obtained in Stage 1.

Stage 2

Genotypes of the 26 candidate SNPs were further verified for all 90 patients using the MassARRAY system from Sequenom (San Diego, USA) according to the iPLEX protocol. The assay was based upon the annealing of a primer adjacent to the polymorphic site of interest. PCR-primers and extension-primers were designed using the software SeqTool Document v1.0 (IBMS, Taiwan). The addition of a DNA polymerase, plus a cocktail mixture of nucleotides and terminators, allowed extension of the primer through the polymorphic site, and generated a unique mass product. The resultant mass of the primer extension product was then analyzed by using the MassARRAY TyperAnalyzer v3.3 software (Sequenom) to determine the sequence of the nucleotides at the polymorphic site. The primers were designed for two SNPs, rs4954256 and rs16863886 for PCR amplification as follows: 5'-ACGTTGGATGTCTACCGTTTCCCGTATCTC-3' (SEQ ID NO. 3) and 3'-ACGTTGGATGCCATATTGGAGAGT-TAACAG-5' (SEQ ID NO. 4) for rs4954256; 5'-ACGTTG-GATGCTGCTTAAGGCAATGGTGTC-3' (SEQ ID NO. 5) and 3'-ACGTTGGATGTTACTTTGGCCCTTCTGTCC-5' (SEQ ID NO. 6) for rs16863886. For these two SNPs, the following PCR conditions were used: 0.5 mM of each primer, 200 mM dNTP, 2.5 units of Taq polymerase, a standard polymerase buffer supplied with enzyme (1.5 mM MgCl2), and 150 ng of genomic DNA. The total volume of the PCR mix was 25 ml. The PCR temperature program was: 95° C. denaturation for 5 min; 35 cycles of 1 min each at 95° C., 1.75 min at 55° C., and 1.75 min at 72° C.; and a final extension run at 72° C. for 10 min. The PCR products were run on a 6% agarose gel at 50 W for 30 min.

Classification of SNPs was manually determined by the MassARRAY TyperAnalyzer v3.3 software (Sequenom, San Diego, USA). Independent Fisher's exact tests were performed for the remaining 60 samples (in addition to the 30 samples in Stage 1). No significant differences were observed between these two populations (data not shown). Therefore, data from all 90 samples were pooled to gain higher statistical power in stage 2. The mean ages were not significantly different between complete and poor responders in both stage 1 and 2 (data not shown). In addition, none of the clinical characteristics, including cigarette smoking, alcohol consumption, and betel nut chewing, were significantly different between complete and poor responders, and thus were not included in further analyses (data not shown). Genotypes of the 30 patients in stage 1 were verified by Sequenom data; and 8 SNPs with high replication error or low call rate were excluded for further analysis. Samples in stage 2 were consisted of the 30 patients and the remained 60 patients.

Further, a Bonferroni correction was used in Stage 2 in order to address the issue of multiple testing. After correction, results of the additive models showed that two SNPs, rs4954256 and rs16863886, were significantly associated with the CCRT response (rs4954256: OR=3.84, 95% CI=1.56-9.43, p-value=0.002; rs16863886: OR=4.54, 95% CI=1.81-11.40, p-value=9×10$^{-4}$). Table 5 lists statistic data of the 18 candidate SNPs in Stages 1 and 2.

9.43). In addition, based on the additive model, the Leave-On-Out Cross Validation (LOOCV) accuracy for predicting the CCRT response was 64.37% for rs4954256 (56 out of 87 patients) and 68.89% for rs16863886 (62 out of 90 patients). Combining both SNPs together increased the prediction accuracy to 72.4% (63 out of 87 patients). The sensitivity (correctly predicting the nonresponders) and specificity (correctly predicting the responders) of this study was 70% and 75%, respectively. The positive prediction value was 71% and negative prediction value was 73%. The regression coefficients of rs4954256 and rs16863886 were 1.3572 and 1.5745 respectively, indicating that the probability of a complete CCRT response increased as the number of minor alleles increased. These results demonstrated that rs4954256 and rs16863886 were strongly associated with CCRT response in ECa patients and can be utilized in predicting CCRT responses.

This is the first two-stage GWAS to identify SNPs with a high accuracy for predicting the CCRT response in treating ECa. Two SNPs, rs4954256 and rs16863886, were found significantly associated with a complete CCRT response (as

TABLE 5

| SNP | location | gene | Minor allele | stage 1* (n = 30) p-value§§ | stage 2** (n = 90) MAF§ Complete responders | stage 2** (n = 90) MAF§ Poor responders | p-value§§ | OR (95% CI)× |
|---|---|---|---|---|---|---|---|---|
| Rs12713098 | 2p16.3 | XRXN1 | A | 7.64 × 10$^{-5}$ | 0.500 | 0.3667 | 0.092 | 1.66 (0.87-3.17) |
| rs4954256 | 2q21.3 | ZRANB3 | C | 3.85 × 10$^{-5}$ | 0.2841 | 0.0930 | 0.002 | 3.84 (1.56-9.43) |
| rs16863886 | 2q36.1 | intergenic | G | 4.75 × 10$^{-7}$ | 0.2841 | 0.0870 | 9 × 10$^{-4}$ | 4.54 (1.81-11.40) |
| Rs4284824 | 2q37.1 | INPP5D | C | 5.35 × 10$^{-5}$ | 0.3182 | 0.4651 | 0.062 | 0.54 (0.29-1.01) |
| Rs4697204 | 4p15.31 | intergenic | G | 1.02 × 10$^{-4}$ | 0.4886 | 0.3256 | 0.032 | 1.98 (1.05-3.74) |
| Rs1876266 | 4p16.1 | intergenic | V | 1.70 × 10$^{-4}$ | 0.3068 | 0.1413 | 0.012 | 2.88 (1.30-6.37) |
| Rs1440971 | 7q32.1 | intergenic | C | 1.73 × 10$^{-5}$ | 0.2045 | 0.1047 | 0.093 | 1.99 (0.88-4.54) |
| Rs1630140 | 9q22.2 | intergenic | C | 1.31 × 10$^{-4}$ | 0.1364 | 0.3023 | 0.010 | 0.32 (0.14-0.74) |
| Rs1805740 | 12p31.13 | PHC1 | C | 6.31 × 10$^{-4}$ | 0.2955 | 0.2093 | 0.224 | 1.53 (0.78-3.00) |
| Rs4240039 | Xp11.4 | intergenic | G | 7.97 × 10$^{-4}$ | 0.1364 | 0.2558 | 0.057 | 0.68 (0.39-1.17) |
| Rs4830776 | Xp22.2 | intergenic | C | 1.23 × 10$^{-4}$ | 0.2045 | 0.3571 | 0.028 | 0.68 (0.42-1.10) |
| Rs5937044 | Xq13.1 | intergenic | A | 1.61 × 10$^{-5}$ | 0.2954 | 0.2791 | 0.868 | 1.04 (0.65-1.66) |
| Rs927142 | Xq21.31 | intergenic | G | 1.55 × 10$^{-5}$ | 0.5 | 0.444 | 1 | 1.12 (0.73-1.85) |
| Rs5990542 | Xq21.33 | intergenic | C | 1.31 × 10$^{-4}$ | 0.5227 | 0.4286 | 0.226 | 1.21 (0.79-1.85) |
| Rs5910842 | Xq24 | intergenic | A | 3.56 × 10$^{-7}$ | 0.5 | 0.3043 | 0.010 | 1.41 (0.92-2.15) |
| Rs10521750 | Xq25 | intergenic | C | 1.91 × 10$^{-6}$ | 0.5682 | 0.3810 | 0.015 | 1.46 (0.95-2.25) |
| rs5951775 | Xq27.3 | intergenic | T | 1.68 × 10$^{-5}$ | 0.1591 | 0.0698 | 0.095 | 1.59 (0.78-3.24) |
| rs1202918 | Xq28 | intergenic | A | 4.53 × 10$^{-5}$ | 0.5114 | 0.3478 | 0.035 | 1.41 (0.92-2.15) |

§MAF denotes the minor allele frequency.
§§p-values were obtained from Fisher's exact test.
*p-values were calculated based on data from 30 patients using microarrays.
**Results in stage 2 were calculated based on all 90 samples examined by mass spectrometry.
×OR denotes odds ratio and was calculated using the additive model.

In addition to Fisher's exact test, Cochran-Armitage trend test was performed to confirm that rs4954256 (p-value=0.002) and rs16863886 (p-value=6×10$^{-4}$) were significantly associated with the CCRT response as the minor allele number increased. SNP rs16863886 is significantly associated with a 4.54-fold risk of complete CCRT response [95% confidence interval (CI)=1.81-11.40] as the number of minor allele increased; and SNP rs4954256 is associated with a 3.84-fold risk of complete CCRT response (95% CI=1.56- the minor allele number increased) and provided a high level of prediction accuracy (72.41%). Such germline polymorphisms determined from blood samples do not change over time. They are very stable, in contrast to somatic mutations obtained from tumor tissue, which change as the disease progresses. The use of the two SNPs according to the invention is helpful in predicting an ECa patient's the response to CCRT and then determining the most appropriate treatment for the patient based on the result of the prediction.

We claim:

1. A method of predicting an increased likelihood of response of a human patient with esophageal cancer to radiochemotherapy and subsequent esophagectomy, wherein the radiochemotherapy comprises radiation in conjunction with cisplatin, 5-fluorouracil and/or paciltaxtel, comprising:
   obtaining a sample from the human patient with esophageal cancer;
   detecting in the sample the presence of a cytosine at the polymorphic position of rs4954256 and the presence of a guanine at the polymorphic position of rs16863886; and
   predicting the human patient with the cytosine at the polymorphic position of rs4954256 and/or the guanine at the polymorphic position of rs16863886 has an increased likelihood of responding to radiochemotherapy and subsequent esophagectomy than a subject without the cytosine at the polymorphic position of rs4954256 and/or the guanine at the polymorphic position of rs16863886.

2. The method of claim 1, further comprising providing a first pair of primers having the sequence of SEQ ID NOS: 3 and 4, respectively, to detect the cytosine at the polymorphic position of rs4954256.

3. The method of claim 1, further comprising providing a second pair of primers having the sequence of SEQ ID NOS: 5 and 6, respectively, to detect the guanine at the polymorphic position of rs16863886.

* * * * *

SEQUENCE LISTING

<160> NUMBER OF SEQ ID NOS: 6

<210> SEQ ID NO 1
<211> LENGTH: 52
<212> TYPE: DNA
<213> ORGANISM: Homo sapiens
<220> FEATURE:
<221> NAME/KEY:
<222> LOCATION: (1)..(52)

<400> SEQUENCE: 1
atattggaga gttaacagag aatgccyaaa actggaaaaa caaaaacttc aa          52

<210> SEQ ID NO 2
<211> LENGTH: 52
<212> TYPE: DNA
<213> ORGANISM: Homo sapiens
<220> FEATURE:
<221> NAME/KEY:
<222> LOCATION: (1)..(52)

<400> SEQUENCE: 2
aatggtgtcc cttgaaggct atctgtytgc ttttggataa aatggacaga ag          52

<210> SEQ ID NO 3
<211> LENGTH: 30
<212> TYPE: DNA
<213> ORGANISM: Artificial Sequence
<220> FEATURE:
<223> OTHER INFORMATION: primer for rs4954256

<400> SEQUENCE: 3
acgttggatg tctaccgttt cccgtatctc                                    30

<210> SEQ ID NO 4
<211> LENGTH: 30
<212> TYPE: DNA
<213> ORGANISM: Artificial Sequence
<220> FEATURE:
<223> OTHER INFORMATION: primer for rs4954256

<400> SEQUENCE: 4
gacaattgag aggttatacc gtaggttgca                                    30

<210> SEQ ID NO 5
<211> LENGTH: 30
<212> TYPE: DNA
<213> ORGANISM: Artificial Sequence
<220> FEATURE:
<223> OTHER INFORMATION: primer for rs16863886

<400> SEQUENCE: 5
acgttggatg ctgcttaagg caatggtgtc                                    30

<210> SEQ ID NO 6
<211> LENGTH: 30
<212> TYPE: DNA
<213> ORGANISM: Artificial Sequence
<220> FEATURE:
<223> OTHER INFORMATION: primer for rs16863886

<400> SEQUENCE: 6
cctgtcttcc cggtttcatt gtaggttgca                                    30